United States Patent
Cross et al.

(10) Patent No.: US 11,915,804 B2
(45) Date of Patent: Feb. 27, 2024

(54) INTEGRATED REPORT

(71) Applicant: CERNER INNOVATION, INC., Kansas City, KS (US)

(72) Inventors: Lori N. Cross, Kansas City, MO (US); Rob Helton, Shawnee, KS (US); Heather Rapp, Kansas City, KS (US); Trent Ahlenius, Blue Springs, MO (US); John Moore, Kansas City, KS (US); Lisa Pastine, Shawnee, KS (US); Nicole McReeves, Kansas City, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 178 days.

(21) Appl. No.: 17/468,828

(22) Filed: Sep. 8, 2021

(65) Prior Publication Data

US 2022/0157420 A1 May 19, 2022

Related U.S. Application Data (60) Provisional application No. 63/114,613, filed on Nov. 17, 2020.

(51) Int. Cl.
*G16H 10/60* (2018.01)
*G06F 40/134* (2020.01)
*G06F 40/186* (2020.01)
*G16H 80/00* (2018.01)

(52) U.S. Cl.
CPC .......... *G16H 10/60* (2018.01); *G06F 40/134* (2020.01); *G06F 40/186* (2020.01); *G16H 80/00* (2018.01)

(58) Field of Classification Search
None
See application file for complete search history.

(56) References Cited

U.S. PATENT DOCUMENTS

| | | | | |
|---|---|---|---|---|
| 7,711,581 | B2 * | 5/2010 | Hood | G16H 15/00 600/300 |
| 8,286,071 | B1 * | 10/2012 | Zimmerman | G16H 10/60 704/235 |
| 8,632,485 | B2 * | 1/2014 | Schlaeper | A61M 1/16 604/4.01 |
| 11,288,319 | B1 * | 3/2022 | Das | G06F 40/186 |
| 11,605,448 | B2 * | 3/2023 | Owen | G06F 40/40 |
| 2005/0288965 | A1 * | 12/2005 | Van Eaton | G16H 40/20 705/2 |
| 2007/0169021 | A1 * | 7/2007 | Huynh | G16H 15/00 717/136 |
| 2008/0103833 | A1 * | 5/2008 | Miglietta | G16H 50/20 705/3 |
| 2010/0138239 | A1 * | 6/2010 | Reicher | G06Q 10/10 715/764 |

(Continued)

*Primary Examiner* — Howard Cortes
(74) *Attorney, Agent, or Firm* — Invoke (57) ABSTRACT

Systems, methods, and storage media useful in a healthcare computing platform to build and publish an integrated medical consultation report to a patient's primary electronic medical record are provided. The integrated medical consultation report presents up-to-date objective medical factors from the patient's medical record concurrently with a subjective medical summary from an authoring clinician. The integrated medical consultation report is stored as a unique medical document in the patient's primary electronic record.

25 Claims, 5 Drawing Sheets

(56) References Cited

U.S. PATENT DOCUMENTS

| | | | | |
|---|---|---|---|---|
| 2011/0004852 A1* | 1/2011 | Baugh | ................... | G16H 10/60 |
| | | | | 715/862 |
| 2011/0071852 A1* | 3/2011 | Sirleaf | ................... | G06Q 10/00 |
| | | | | 705/3 |
| 2011/0191114 A1* | 8/2011 | Bhagwan | ............... | G16H 10/20 |
| | | | | 707/769 |
| 2011/0301978 A1* | 12/2011 | Shiu | ....................... | G16H 10/60 |
| | | | | 705/3 |
| 2011/0301982 A1* | 12/2011 | Green, Jr. | .............. | G16H 40/67 |
| | | | | 705/3 |
| 2012/0109686 A1* | 5/2012 | Higbie | ................... | G16H 15/00 |
| | | | | 705/3 |
| 2016/0048647 A1* | 2/2016 | Aizawa | .................. | G16H 70/20 |
| | | | | 705/2 |
| 2018/0190369 A1* | 7/2018 | Wolz | ....................... | G16Z 99/00 |
| 2019/0027149 A1* | 1/2019 | Vogel | ..................... | G16H 10/60 |
| 2019/0122750 A1* | 4/2019 | Ghosh | ................... | G16H 10/40 |
| 2019/0295695 A1* | 9/2019 | Dandala | ................ | G16H 10/20 |
| 2019/0320898 A1* | 10/2019 | Dirghangi | ................ | A61B 3/15 |
| 2020/0143084 A1* | 5/2020 | Rosenberg | ............. | G16H 30/20 |
| 2020/0364182 A1* | 11/2020 | Threlkeld | .............. | G16H 15/00 |
| 2021/0233629 A1* | 7/2021 | Gray | ....................... | G06F 16/275 |
| 2022/0084664 A1* | 3/2022 | Ginsburg | ............... | G16H 15/00 |

\* cited by examiner

| LEUKEMIA-LYMPHOMA INTEGRATED REPORT |
| --- |
| A SUMMARY OF THE PATIENT'S CLINICAL AND ANATOMIC PATHOLOGY LABORATORY RESULTS INDICATE THAT THE PATIENT HAS... |
|  |

305

330 — BONE MARROW REPORT COLLECTED 12/1/2019 09:00  *NEW INFORMATION AVAILABLE* — 332

DIAGNOSIS:

CLINICAL INFORMATION:

GROSS DESCRIPTION:

335 CBC WITH DIFF COLLECTED 12/5/2019 07:31

| WHITE CELL COUNT | 7.2 | X10^3/UL | (5.0-14.5) |  |
| --- | --- | --- | --- | --- |
| RED CELL COUNT | 3.89 | X10^6/UL | (3.70-5.30) |  |
| HEMOGLOBIN | 10.7 | G/DI | (10.5-13.5) |  |
| HEMATOCRIT | 34 | % | (33-49) |  |

CYTOGENETICS REPORT COLLECTED 12/1/2019 09:00

KARYOTYPE
46.XY

COMMENT / INTERPRETATION:

INTEGRATED REPORT

310 DIAGNOSIS: LYMPHOPROLIFERATIVE DISORDER, HODGINS LYMPHOMA, SECONDARY TO 17 YEAR IMMUNOSUPPRESSIVE TREATMENT FOR INFLAMMATORY BOWEL DISEASE. HISTORY: 40 YO MALE WITH ILEOCOLIC NON-STENOTIC CROHN'S DISEASE SINCE 200 TREATED WITH AZATHIOPRINE 100 MG OD (2MG/KG)

MEDICATIONS HISTORY

325  AZATHIOPRINE 100 MG

320 ABDOMINAL CT

315 PATHOLOGY – FINE NEEDLE ASPIRATE (400X)

REFERENCES

*FIG. 3.*

| INDUSTRY | AUTHOR'S AREA / DEPARTMENT | INTEGRATED REPORT | REFERENCED FACTORS |
|---|---|---|---|
| HEALTHCARE | CLINICAL LABORATORY (ANATOMIC PATHOLOGY) | LEUKEMIA/ LYMPHOMA CONSULTATION | - BONE MARROW PATHOLOGY REPORT<br>- PERIPHERAL BLOOD CBC (COMPLETE BLOOD COUNT)<br>- CYTOGENETICS REPORT<br>- FISH REPORT<br>- FLOW CYTOMETRY REPORT<br>- NEXT-GEN SEQUENCING REPORT<br>- TARGETED GENETIC SEQUENCING REPORT |
| HEALTHCARE | CLINICAL LABORATORY (MICROBIOLOGY) | INFECTIOUS DISEASE CONSULTATION | - MICROBIOLOGY CULTURE REPORT(S)<br>- VIROLOGY REPORT(S)<br>- INFECTIOUS DISEASE MOLECULAR DIAGNOSTICS RESULTS<br>- HISTORY & PHYSICAL EXAM<br>- TRAVEL HISTORY |
| HEALTHCARE | PATIENT CARE AND THE CLINICAL LABORATORY (BLOOD BANK) | TRANSFUSION REACTION CONSULTATION | - PRE-TRANSFUSION VITAL SIGNS<br>- DURING TRANSFUSION VITAL SIGNS<br>- POST-TRANSFUSION VITAL SIGNS<br>- CLERICAL CHECK FINDINGS<br>- POST-TRANSFUSION HEMOGLOBIN VALUE<br>- POST-TRANSFUSION DAT VALUE<br>- POST-TRANSFUSION ABO/RH VALUE<br>- POST-TRANSFUSION HAPTOGLOBIN VALUE<br>- POST-TRANSFUSION BILLIRUBIN VALUE<br>- POST-TRANSFUSION LDH VALUE<br>- POST-TRANSFUSION URINE HEMOGLOBIN VALUE<br>- POST-TRANSFUSION CROSSMATCH VALUE<br>- MEDICATION |

INTEGRATED REPORT

CROSS-REFERENCE TO RELATED APPLICATION

This application claims the benefit of U.S. Provisional Application No. 63/114,613, titled "Integrated Report," filed Nov. 17, 2020, which is hereby expressly incorporated by reference in its entirety.

SUMMARY

Oftentimes, a patient is seeing a number of clinicians and having a variety of tests completed during an in-patient hospitalization or a complex ambulatory visit. However, the subjective textual summary of a clinicians' consultation with the patient is maintained separate from the objective factors considered from a patient's primary record.

As such, anyone viewing the subjective summary of a clinician's consultation would have to access multiple screens and applications to view the different objective factors. Furthermore, in some instances, the textual summaries of the clinicians maintained in a patient's primary record may not even indicate any objective factors taken into account by the clinicians when creating the subjective textual summary of the consultation with the patient.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present disclosure is defined by the claims as supported by the Specification, including the Detailed Description.

System, method and computer readable media for generating, for clinicians while viewing the primary medical record for a patient being treated, a graphical user interface that presents a user-interactive medical consultation report template are provided. The user-interactive template has at least one subjective section for receiving subjective assessment of the patient from the clinicians. The user-interactive template further includes multiple objective sections for receiving input from the clinicians with objective medical factors considered from the primary medical record and pointer associated with the objective medical factors. Multiple objective medical factors and associated pointers are received from the authoring clinicians. The objective medical factors and associated pointers are the objective factors considered by the authoring clinicians when making a subjective assessment or opinion. User input of subjective assessment of the patient is received via the graphical user interface. The subjective assessment of the patient is stored for the medical consultation report for the patient. Links or pointers are embedded for each objective medical factor in the medical consultation report to the objective medical factors residing in a primary medical record for the patient. The integrated medical consultation report with the subjective assessment and embedded links for the patient is stored in the patient's primary record as a unique document.

In one embodiment, a request from a viewing clinician to view the integrated medical consultation report for the patient is received while viewing the patient's primary record. The stored template is accessed with subjective assessment and the embedded pointers. The embedded pointers are utilized to access and load data into the template for the current objective medical factors from the patient's primary record. A graphical user interface is generated in the integrated medical consultation report with the subjective assessment of the patient for the medical consultation report and the data for the medical factors from the patient's primary record. If the objective medical factors are unavailable in the patient's primary record, placeholders on the graphical user interface are generated for data for one or more of the medical factors from the patient's primary record that do not yet have results or values. The viewing user is notified when the one or more of the medical factors missing from the integrated medical consultation report are received in the patient's primary record. The viewing clinician may view the results and republish the integrated medical consultation report in the patient's primary medical record.

BRIEF DESCRIPTION OF THE DRAWINGS

Illustrative aspects of the present invention are described in detail below with reference to the attached drawing figures, and wherein.

DETAILED DESCRIPTION

The subject matter of the present invention is being described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Terms should not be interpreted as implying any particular order among or between various steps herein disclosed unless and except when the order of individual steps is explicitly described. As such, although the terms "step" and/or "block" can be used herein to connote different elements of system and/or methods, the terms should not be interpreted as implying any particular order and/or dependencies among or between various components and/or steps herein disclosed unless and except when the order of individual steps is explicitly described. The present disclosure will now be described more fully herein with reference to the accompanying drawings, which may not be drawn to scale and which are not to be construed as limiting. Indeed, the present invention can be embodied in many different forms and should not be construed as limited to the aspects set forth herein. Further, it will be apparent from this Detailed Description that the technological solutions disclosed herein are only a portion of those provided by the present invention. As such, the technological problems, solutions, advances, and improvements expressly referenced and explained herein should not be construed in a way that would limit the benefits, improvements, and/or practical application of the discussed aspects of the present invention.

The healthcare computing platform of embodiments of the invention advances clinicians' ability to build an integrated medical consultation report with both a subjective assessment and pointers to objective factors considered from the patient's primary medical record. The healthcare computing platform allows for more accurate data to be included in a subjective medical consultation report for a patient and point to the objective medical factors in the patient's medical record without cutting and pasting the data for the factors into the report. This allows for current, most up-to-date objective medical factors to be included in the integrated medical consultation report for a subsequent viewing clinicians.

Previous solutions included cutting and pasting static text of objective medical factors by author clinicians into a medical consultation report. As such, when viewing clinicians viewed the report, they would not necessarily know any or all of the objective medical factors reviewed by the author clinicians of the integrated medical consultation report. Further, viewing clinicians would not know whether the results or values for the objective medical factors had been received, were current, or had been updated. Viewing clinicians would have to perform numerous searches and clicks in the patient's primary medical record to find the current or updated results or values for objective medical factors considered by the author clinician.

The healthcare computing platform allows an authoring clinician to build an integrated medical consultation report with a subject summary and pointers to the object medical factors considered by author clinicians. This provides a number of improvements and advantages to previous solutions in the electronic medical record context. First, it allows a subsequent clinicians viewing the integrated medical consultation report to see all the objective medical factors considered by an authoring clinician. Additionally, it updates the results and values for the objective medical factors from the patient's primary medical record as they are received into the primary medical record. Thus, within the unique medical consultation document, missing or updated results and values may be automatically and accurately updated in the medical consultation report. A notification is provided to the viewing and/or authoring clinicians that missing or updated results/values have been entered into the patient's primary record. The viewing and/or authoring clinicians can see there are new or updated results/values and choose to use those values in a subsequent updated medical consultation report.

Aspects of the invention provide automatic, without user intervention, seamless updating of electronic medical consultation reports. The healthcare computing platform can access objective medical factors across venues of care, including laboratory, radiology, pathology, genetics, infectious disease, respiratory, blood bank, ambulatory, acute, emergency, and specialized care. The healthcare computing platform allows viewing and authoring clinicians to evaluate new and updated values and results for the patient as part of the integrated medical consultation report without having to spend time finding the values and results in other parts of the patient's primary medical record. It also reduces the need for authoring clinicians to cut and paste objective medical factors into a medical consultation report and keeps the results and values consistent across the patient's primary medical record and medical consultation reports. It prevents error on behalf of a clinician by reviewing out of date or stale results and values for the patient. The subjective assessment by an authoring clinician is displayed in a side-by-side with the objective medical factors from the patient's primary record to be more conducive and intuitive to cognitive comparison needed when clinicians are evaluating subjective and objective data.

In one aspect, graphical user interfaces of the healthcare computing environment allow viewing clinicians to view other clinicians' subjective assessments along with the objective medical factors considered. This allows better and more seamless care of the patient as the viewing clinicians do not have to click and search through the patient's primary record to understand what has previously been evaluated for the patient and where medical assessments currently stand for the patient.

Figure 1:
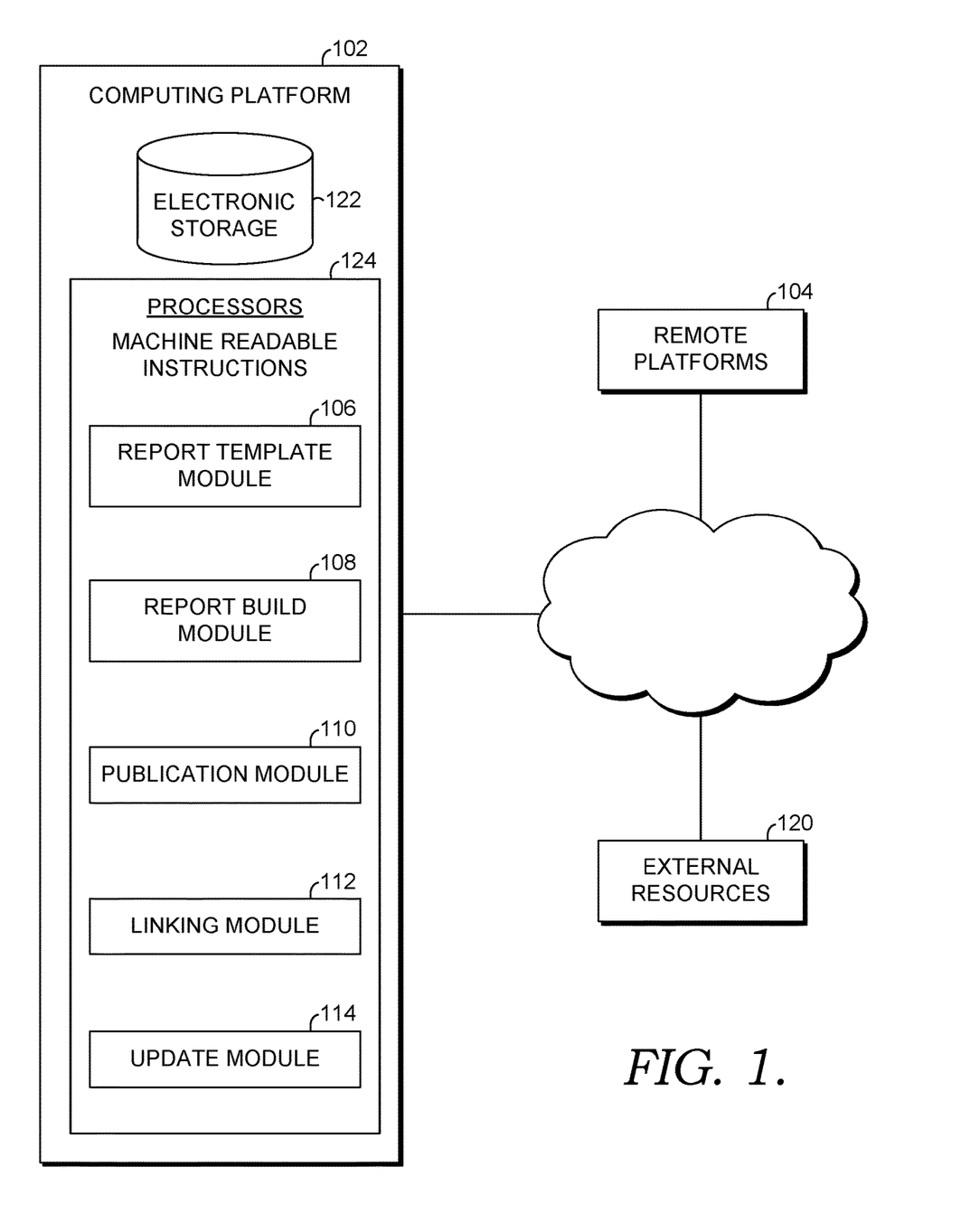
FIG. 1 illustrates a healthcare computing platform, in accordance with aspects of the invention.

FIG. 1 illustrates a system 100 configured to be useful in a computer healthcare system to consume clinical quality language queries in a programmatic manner, in accordance with one or more implementations. In some implementations, system 100 may include one or more healthcare cloud computing platforms 102. Computing platform(s) 102 may be configured to communicate with one or more remote platforms 104 according to a client/server architecture, a peer-to-peer architecture, and/or other architectures. Remote platform(s) 104 may be configured to communicate with other remote platforms via computing platform(s) 102 and/or according to a client/server architecture, a peer-to-peer architecture, and/or other architectures. Users may access system 100 via remote platform(s) 104.

In some implementations, computing platform(s) 102, remote platform(s) 104, and/or external resource(s) 120 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which computing platform(s) 102, remote platform(s) 104, and/or external resource(s) 120 may be operatively linked via some other communication media.

A given remote platform 104 may include one or more processors configured to execute computer program modules. The computer program modules may be configured to enable an expert or user associated with the given remote platform 104 to interface with system 100 and/or external resource(s) 120, and/or provide other functionality attributed herein to remote platform(s) 104. By way of non-limiting example, a given remote platform 104 and/or a given computing platform 102 may include one or more of a server, a desktop computer, a laptop computer, a handheld computer, a tablet computing platform, a NetBook, a Smartphone, a gaming console, and/or other computing platforms.

External resources 120 may include sources of information outside of system 100, external entities participating with system 100, and/or other resources.

Computing platform(s) 102 may include electronic storage 122, one or more processors 124, and/or other components. Computing platform(s) 102 may include communication lines, or ports to enable the exchange of information with a network and/or other computing platforms. Illustration of computing platform(s) 102 in FIG. 1 is not intended to be limiting. Computing platform(s) 102 may include a plurality of hardware, software, and/or firmware components operating together to provide the functionality attributed herein to computing platform(s) 102. For example, computing platform(s) 102 may be implemented by a cloud of computing platforms operating together as computing platform(s) 102.

Electronic storage 122 may comprise non-transitory storage media that electronically stores information. The electronic storage media of electronic storage 122 may include one or both of system storage that is provided integrally (i.e., substantially non-removable) with computing platform(s) 102 and/or removable storage that is removably connectable to computing platform(s) 102 via, for example, a port (e.g., a USB port, a firewire port, etc.) or a drive (e.g., a disk drive, etc.). Electronic storage 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 122 may include one or more virtual storage resources (e.g., cloud storage, a virtual private network, and/or other virtual storage resources). Electronic storage 122 may store software algorithms, information determined by processor(s) 124, information received from computing platform(s) 102, information received from remote platform(s) 104, and/or other information that enables computing platform(s) 102 to function as described herein.

Processor(s) 124 may be configured to provide information processing capabilities in computing platform(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same device, or processor(s) 124 may represent processing functionality of a plurality of devices operating in coordination. Processor(s) 124 may be configured to execute modules 106, 108, 110, 112, and/or 114, and/or other modules. Processor(s) 124 may be configured to execute modules 106, 108, 110, 112, and/or 114, and/or other modules by software; hardware; firmware; some combination of software, hardware, and/or firmware; and/or other mechanisms for configuring processing capabilities on processor(s) 124. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although modules 106, 108, 110, 112, and/or 114 are illustrated in FIG. 1 as being implemented within a single processing unit, in implementations in which processor(s) 124 includes multiple processing units, one or more of modules 106, 108, 110, 112, and/or 114 may be implemented remotely from the other modules. The description of the functionality provided by the different modules 106, 108, 110, 112, and/or 114 described below is for illustrative purposes, and is not intended to be limiting, as any of modules 106, 108, 110, 112, and/or 114 may provide more or less functionality than is described. For example, one or more of modules 106, 108, 110, 112, and/or 114 may be eliminated, and some or all of its functionality may be provided by other ones of modules 106, 108, 110, 112, and/or 114. As another example, processor(s) 124 may be configured to execute one or more additional modules that may perform some or all of the functionality attributed below to one of modules 106, 108, 110, 112, and/or 114.

Computing platform(s) 102 may be configured by machine-readable instructions. Machine-readable instructions may include one or more instruction modules. The instruction modules may include computer program modules. The instruction modules may include one or more of record retrieval module 106, state machine module 108, deduplication module 110, rules module 112, ranking engine module 114, and/or other instruction modules.

Platform 102 is a clinical electronic medical record (EMR) platform, such as Cerner HealtheIntent™ and/or Cerner Millennium™. External resources 120 include third-parties, such as health information exchange (HIE), immunization registry, governmental healthcare registry, pharmaceutical registry, and third-party electronic medical record provider. Clinical medical data for individuals exists in a variety of different sources, such as National Exchange thru CommonWell and Carequality, state/regional HIEs, consumers, consumer devices, hospitals, ambulatory practices, pharmacy claims, and fill data from pharmacy databases, such as Surescripts, state vaccination registries, and other connected venues of care.

Generally, the patient's primary medical record (electronic medical record (EMR) or electronic health record (EHR)) maintained in electronic storage 122 of computing platform 102, is data comprising electronic clinical documents, such as images, clinical notes, orders, summaries, reports, analyses, information received from clinical applications, and medical devices, or other types of electronic medical documentation relevant to a particular patient's condition and/or treatment. The patient data from EMR may persist in a local copy of the patient's EMR or may be stored in a cloud computing environment. Electronic clinical documents may contain various types of information relevant to the condition and/or treatment of a particular patient and can include information relating to, for example, patient identification information, images, alert history, previously consumed neuropsychiatric drugs, culture results, patient-entered information, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information. Further, in some embodiments, patient data stored in the EMR may include patient demographic data, such as age, sex, race, nationality, socioeconomic status, marital status, and employment status and history. This data may further include the patient's insurance information, such as the insurance provider and the type of plan. Additional patient data may include previous and current home and work addresses.

Other types of patient data stored in the EMR may include current patient data and historical patient data. In exemplary aspects, current patient data includes data relating to the patient's labs, vitals, diagnoses, and medications from a current encounter (e.g., a current admission to a healthcare facility, a current visit to an outpatient facility, or a current period of receiving home healthcare services). The current patient data may include a diagnosis and/or treatment (including medications administered or ordered and procedures performed or ordered). During the current encounter, the patient may be diagnosed with or treated for a condition, such as asthma, cancer, or heart disease, for example. Current patient data may further include lab results (e.g., physiological data), including vital sign data, from the current encounter. Historical patient data may include information about the patient's past encounters at the current healthcare facility or other healthcare facilities, past encounters at a post-acute care facility, etc. In some embodiments, historical patient data includes previous diagnoses, medications, and lab results.

Further, the EMR may include patient data received from different sources. In other embodiments, data relating to the patient's current condition and/or patient demographics may be received directly from a user, such as the patient or a care provider, inputting such information into a user device. Patient data for a longitudinal record may come from the patient's EMR or data from third-party databases. Some current patient data, such as patient variable values, may be received from one or more sensors or monitoring devices or directly from a laboratory running the laboratory procedures. Additionally, historical patient information may be received from the patient's EMR and/or from insurance claims data for the patient. For example, data from in-home care services, hospitals, or any healthcare facility may be received. In an alternative embodiment, the patient's history may be received directly from the patient, such as during registration when admitted to a care facility for the current encounter or starting the current care services (such as with in-home care services).

Medical data elements may include patient condition, orders, patient demographic information (age, gender, height, and weight), vital signs, test results, images, medications, medication administration, tasks, facility information, and caregiver information. The database record store 122 includes medical data elements, such as Cerner Millennium™ or Cerner HealtheIntent Longitudinal Record™, and utilizing the modules 106, 108, 110, 112, and 114 data that has been transferred and recorded in database record store 122.

The healthcare computing platform 102 includes report template module 106, report build module 108, publication module 110, linking module 112, and update module 114.

Report template module 106 is configured to access user-interactive medical consultation report template. Report template module 106 provides a wireframe or template for authoring clinicians to build an integrated medical consultation report. The user-interactive template has at least one subjective section for receiving a subjective assessment of a patient from clinicians and multiple objective sections for receiving input from clinicians with objective medical factors considered and a link tag associated with the objective medical factors. Subjective assessment of the patient by clinicians is the opinion or summary of the patient's clinical condition, diagnosis or outcome based on a medical consultation. Objective medical factors comprise patient medical data elements, including, but not necessarily limited to, one or more of laboratory results, pathology reports, microbiology reports, genetic test results, infectious disease test results, patient history, patient images, patient physical examination, patient travel history, patient vital sign values, and radiology results.

Figure 3:
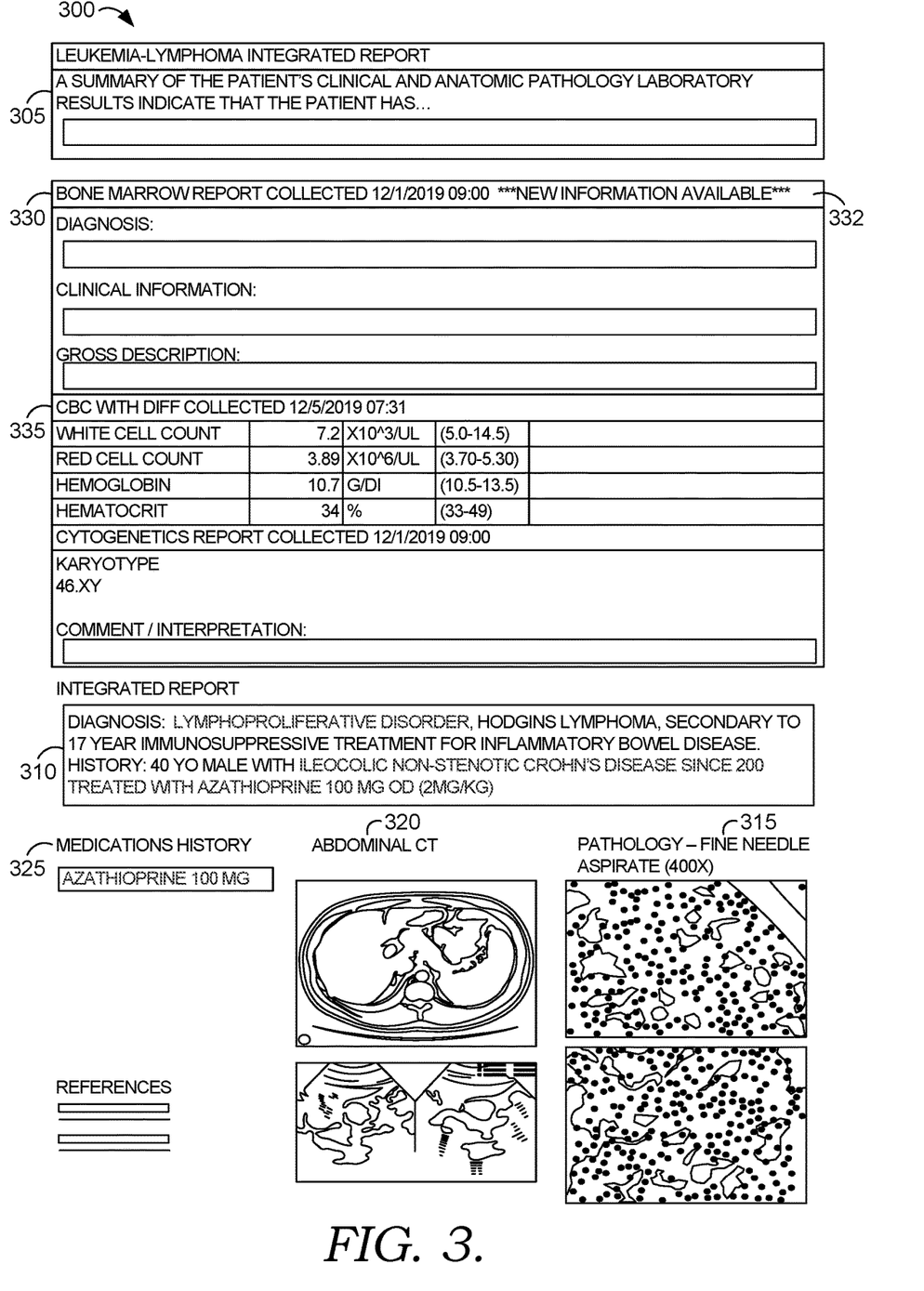
FIG. 3 depicts a graphical user interface displaying an integrated medical consultation report for a patient in accordance with aspects of the invention.

With reference to FIG. 3, an exemplary integrated consultation report 300 is shown. As can be seen in exemplary consultation report 300, there is at least one subjective section 310 for receiving a textual subjective assessment of a patient from authoring clinicians. Exemplary consultation report 300 includes multiple objective sections 330, 335, 315, 320, and 325 with data for objective medical factors considered by the authoring clinicians to formulate the subjective assessment.

Figure 4:
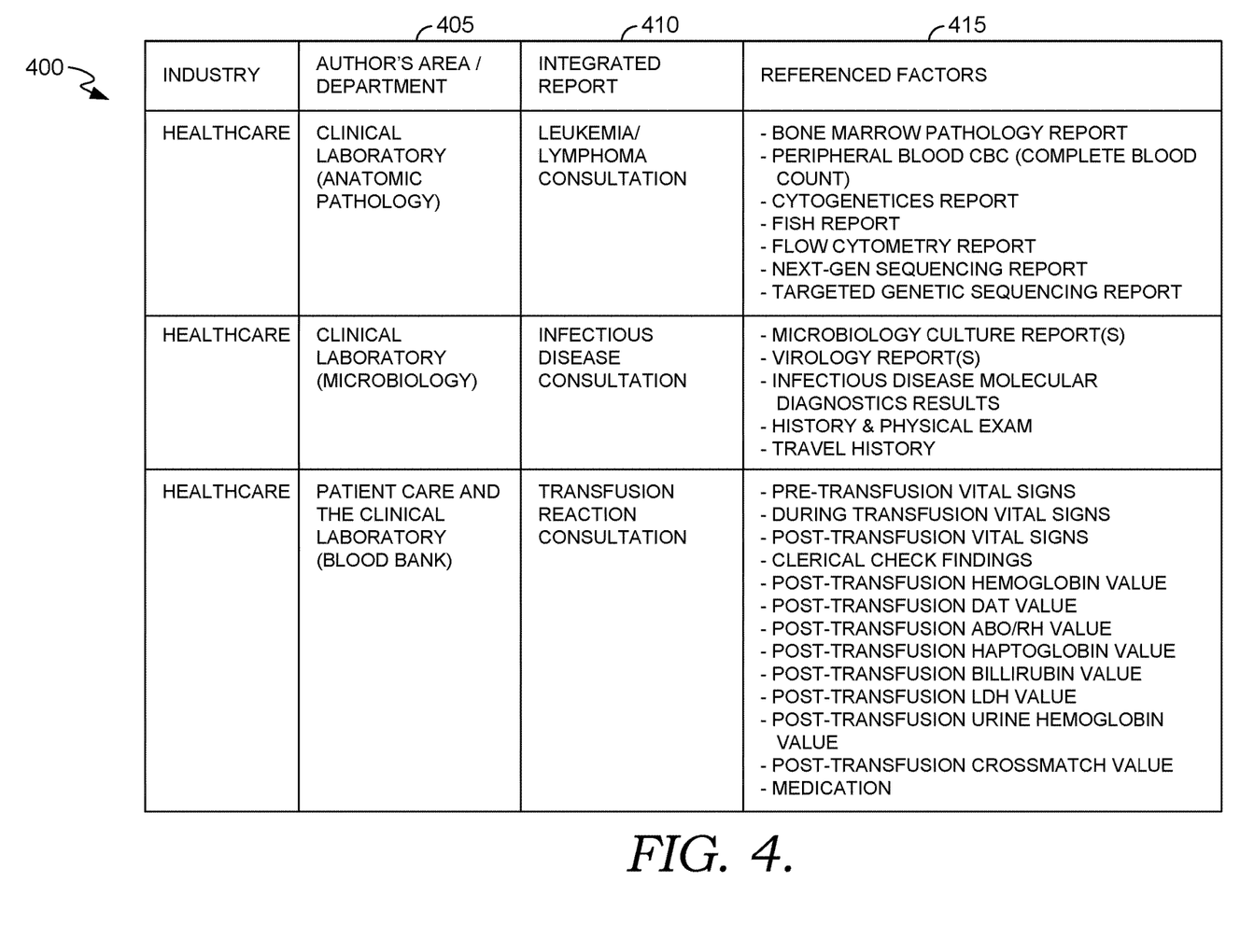
FIG. 4 depicts exemplary medical consultation and objective medical factors for the medical consultation in accordance with aspects of the invention.

From report build module 108 authoring clinicians initiate an integrated medical consultation report. The report template is presented to the authoring clinicians. The authoring clinicians nams the template. For example, with reference to FIG. 4, a clinical laboratory pathologist 405 initiates and names an integrated medical consultation report 400 for leukemia/lymphoma consultation. Report build module 108 names the report and presents the subjective section for textual entry and objective sections for authoring user to select objective factors to be included in the integrated medical consultation report. Report build module 108 presents to the authoring user objective factors recently reviewed by authoring clinicians such that authoring clinicians can choose the objective factors relevant to the consultation report. With reference to FIG. 4, an authoring clinician has recently viewed objective references factors 415 bone marrow pathology report, peripheral blood CBC, cytogenetics report, FISH report, flow cytometry report, next-generation sequencing report, and targeted genetic sequencing report. Authoring clinician may select some or all of the recently reviewed objective factors 415 to include in the integrated medical consultation report.

Figure 5:
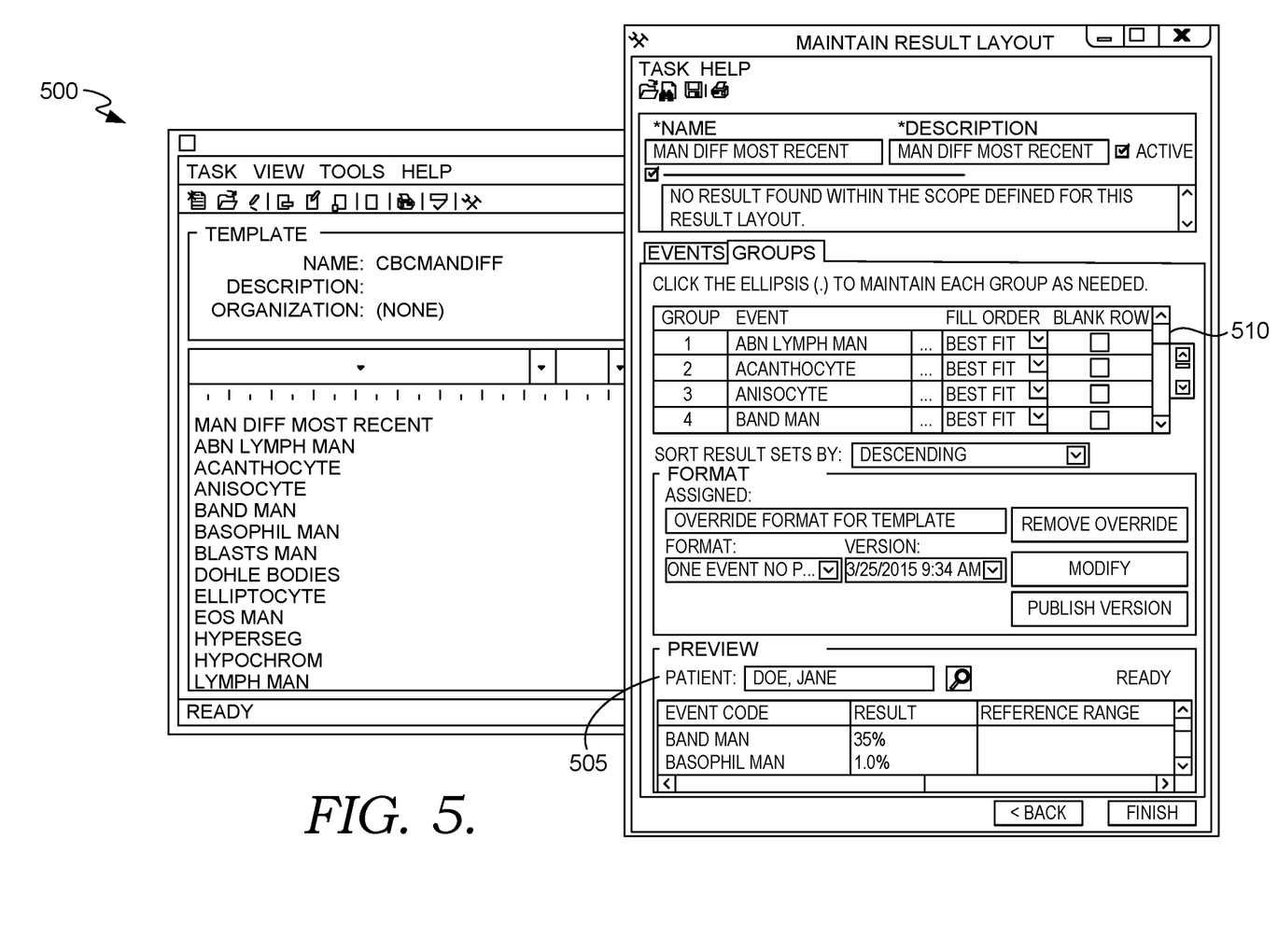
FIG. 5 depicts an exemplary graphical user interface for building an integrated medical consultation report in accordance with aspects of the invention.

In an alternative embodiment, with reference in FIG. 5, the authoring clinicians may select objective factors to be included in an integrated medical consultation report while reviewing the objective factors. For example, in FIG. 5, while reviewing CBC laboratory test results an authoring clinician selects the test results that have been considered and those the authoring clinician believes are relevant to the clinician's subjective textual summary entered into the subjective section of an integrated medical consultation report. For example, while reviewing the CBC laboratory test results for the patient 505 within the patient's primary record (EMR), the authoring clinician finds that patient's results for ABN Lymph Man, Acatocyte, Anisocyte, and Band Man are relevant and should be included in the authoring clinician's integrated medical consultation report.

Additionally, the objective factors selected for the consultation by an authoring clinician may be for clinical orders requested by the authoring clinician or other clinicians to be completed for the patient. As the order may still need to be completed, the pointer for the objective factor is to the clinical order and/or its subsequent results or values when they are entered or received by the patient's primary medical record.

After receiving selection of these objective medical factors, the linking module 112 adds pointers or navigation directions to the selected objective factors within the patient's primary record. The authoring clinician enters his/her textual summary to subjective section of the integrated medical consultation report template. Publication module 110 publishes the integrated report to the patient's primary medical record. Once the clinician has completed entry of the textual summary in the subject section and the selection of objective factors considered, the authoring clinician publishes the integrated report to the patient's primary record. The integrated report is stored as a unique document in the patient's primary record with the identification of the authoring user, the report type, the textual subjective summary, and pointers to objective factors considered for later reference by the authoring clinicians or a viewing clinicians.

Update module 114 receives a request from authoring clinician and/or a viewing clinician to display the integrated consultation report. The request comes from a clinician while viewing the patient's primary record. Update module 114 accesses the stored template with subjective assessment and the embedded pointers. Update module 114 utilizes the embedded pointers to access and load data for the medical factors from the patient's primary record into the template. Update module 114 generates a graphical user interface of the integrated medical consultation report with the subjective assessment of the patient for the integrated medical consultation report and the data for the medical factors from the patient's primary record.

If the authoring clinicians selected objective medical factors that are still awaiting results or values, update module 114 generates placeholders on the graphical user interface for data for one or more of the objective medical factors from the patient's primary record that do not yet have results or values. The placeholders notify the viewing user that the one or more of the objective medical factors from the patient's primary record do not yet have results or values.

Update module 114 is also configured to send alerts and notifications when a result or value has been entered into the patient's primary medical record. For example, if a lab test or pathology report that has not previously been viewed by clinicians is now available within the patient's primary record, an alert depicting the availability of new information is displayed to the clinicians.

With reference to exemplary FIG. 3, authoring clinician has utilized report build module 108 to build integrated medical consultation report 300. The report 300 has been named leukemia-lymphoma integrated medical consultation report 305. The objective factors selected by authoring user for the integrated medical consultation report are bone marrow report 330, CBC with Diff report 335, abdominal CT report 320, pathology aspirate report 315, and medication history report 325 for the patient. Authoring clinician enters a subjective textual summary in subjective section 310 of the report template. The pointers provide a map to the objective factors in the patient's primary medical record.

With reference to FIG. 3, authoring clinician has selected to include the objective medical factor for a bone marrow report for the patient. That value is still outstanding and, as such, update module 114 has generated a placeholder showing bone marrow report 330 is part of the integrated medical consultation report but it has not yet been added and/or viewed by clinicians.

FIG. 3 also depicts an alert that one or more of the objective medical factors selected by the authoring clinician are now available in the patient's primary record. Notification 332, from within the integrated medical consultation report, alerts clinicians there is new or updated information in the patient's medical record for the objective medical factor. The alert may be selected by the clinicians to view the new or updated information for the objective medical factor. In one embodiment, the update module 114 will then give clinicians the option to add the new information to the integrated medical consultation report. The update module 114 provides the option for clinicians to update the subjective summary and/or objective factors and republish the report as a new unique document that is separate from the original integrated medical consultation report but with a historical reference to previous versions of the integrated medical consultation report.

Figure 2:
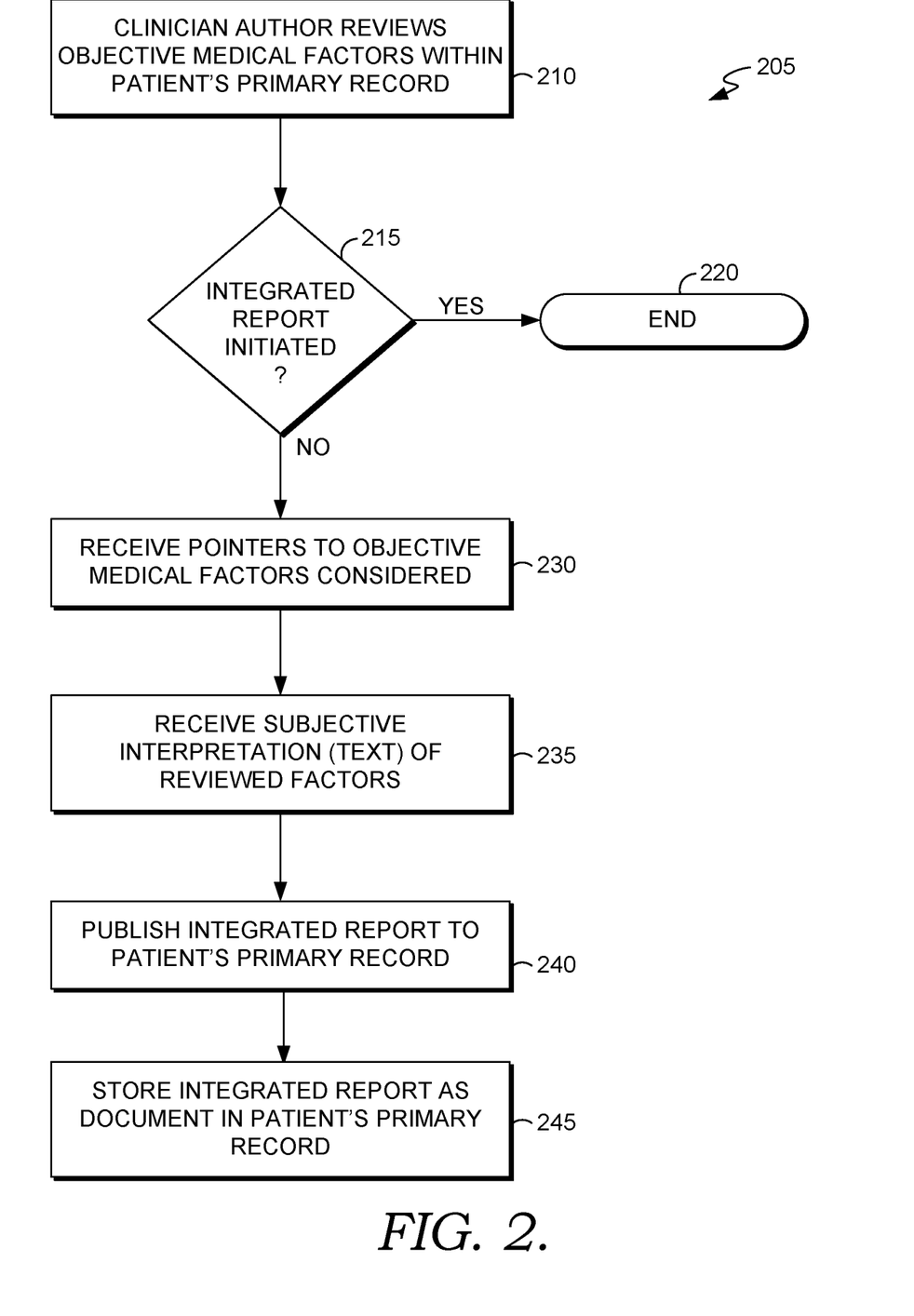
FIG. 2 depicts a flow chart of building an integrated medical consultation report for a patient in accordance with aspects of the invention.

FIG. 2 illustrates a method useful in a healthcare computing platform 102, in accordance with one or more implementations. With reference to FIG. 2, operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not necessarily limiting.

In some implementations, method 205 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

FIG. 2 illustrates method 205, in accordance with one or more implementations. Method 205 may be performed by one or more hardware processors configured by machine-readable instructions including a module that is the same as or similar to build module 108, in accordance with one or more implementations. A method 205 provides objective medical factors to a clinician authoring a medical consultation report. Clinician views medical data for a patient from a patient's primary electronic medical record. Operation 215 triggers the initiation of an integrated report if requested by the authoring clinician. The method 205 ends at operation 220 if if an integrated report has not been initiated. This may occur if clinicians merely want to view a consultation report of platform 102 but does not want to author a report.

When an integrated report is initiation at 215, operation 230 receives a selection of objective medical factors from the authoring clinician. As the authoring clinician has chosen to initiate an integrated medical consultation report, platform 102 is configured to store pointers to the selected objective medical factors for the integrated medical consultation report. Operation 235 receives a textual (or voice to text) medical summary or opinion from the authoring clinician. The medical summary or opinion is a review of the objective medical factors reviewed by the authoring clinician and a medical conclusion. Operation 240 publishes the consultation report to the patient's primary medical record when the clinician selects sign or submit of the integrated medical consultation report. Operation 245 stores the integrated medical consultation report, with the objective medical factor pointers, subjective summary, and authoring clinician identification as a unique document in the patient's primary medical record for access later by the authoring clinician or viewing clinicians.

Although the present technology has been described in detail for the purpose of illustration based on what is currently considered to be the most practical and preferred implementations, it is to be understood such detail is solely for that purpose and the technology is not limited to the disclosed implementations, but, on the contrary, is intended to cover modifications and equivalent arrangements that are within the spirit and scope of the appended claims. For example, it is to be understood the present technology contemplates that, to the extent possible, one or more features of any implementation can be combined with one or more features of any other implementation.

The invention claimed is:

1. One or more non-transitory media storing instructions executable by a processor to initiate operations comprising:

generating, while displaying a primary medical record for a patient, a graphical user interface that presents a template usable for creation of:
(a) a subjective assessment, of the patient, by a clinician; and
(b) one or more objective medical factor indicators, corresponding to one or more objective medical factors in the primary medical record, associated with the subjective assessment and considered by the clinician;
receiving first input for the creation of the one or more objective medical factor indicators, and second input for the creation of the subjective assessment, via the graphical user interface;
embedding, in a user-interactive medical consultation report corresponding to the template, one or more links from the one or more objective medical factor indicators to one or more corresponding objective medical factors in the primary medical record; and
storing an integrated medical consultation report, with the subjective assessment and the embedded one or more links, in the primary medical record as a unique document.

2. The one or more media of claim 1, wherein the operations further comprise: while displaying the primary medical record, receiving a request from a clinician to view the integrated medical consultation report.

3. The one or more media of claim 2, wherein the operations further comprise: accessing the stored integrated medical consultation report with the subjective assessment and the embedded one or more links.

4. The one or more media of claim 3, wherein the operations further comprise: utilizing the embedded one or more links to access and load data for the one or more objective medical factors from the primary medical record into the template.

5. The one or more media of claim 4, wherein the operations further comprise: generating a graphical user interface of the integrated medical consultation report.

6. The one or more media of claim 5, wherein the operations further comprise: generating placeholders on the graphical user interface for data for the one or more objective medical factors from the primary medical record that do not yet have results or values.

7. The one or more media of claim 6, wherein the placeholders are configured to notify the viewing user that the one or more of the objective medical factors from the primary medical record do not yet have results or values.

8. The one or more media of claim 1, wherein the objective medical factors comprise one or more of laboratory results, pathology reports, microbiology reports, genetic test results, infectious disease test results, patient history, patient images, patient physical examination, patient travel history, patient vital sign values, or radiology results.

9. The one or more media of claim 1, wherein the template includes a plurality of objective medical factors, and wherein each of the plurality of the objective medical factors in the template is selectable by the clinician during creation of the integrated medical consultation report.

10. The one or more media of claim 9, wherein each objective medical factor of the plurality of objective medical factors in the template includes a pointer associated with a location of the objective medical factor in the primary medical record.

11. The one or more media of claim 1, wherein the template comprises a drop-down menu including a plurality of objective medical factors that are each selectable by the clinician.

12. The one or more media of claim 1, wherein generating the graphical user interface comprises displaying the template concurrently with displaying the primary medical record.

13. The one or more media of claim 1, wherein the operations further comprise displaying, via the graphical user interface: (a) the subjective assessment of the stored integrated medical consultation report side-by-side with (b) the one or more objective medical factors of the stored integrated medical consultation report.

14. A system comprising: a memory and one or more processors configured by use the memory to execute machine-readable instructions to initiate operations comprising:
generating, while displaying a primary medical record for a patient, a graphical user interface that presents a template usable for creation of:
(a) a subjective assessment, of the patient, by a clinician; and
(b) one or more objective medical factor indicators, corresponding to one or more objective medical factors in the primary medical record, associated with the subjective assessment and considered by the clinician;
receiving first input for the creation of the one or more objective medical factor indicators, and second input for the creation of the subjective assessment, via the graphical user interface;
embedding, in a user-interactive medical consultation report corresponding to the template, one or more links from the one or more objective medical factor indicators to one or more corresponding objective medical factors in the primary medical record; and
storing an integrated medical consultation report, with the subjective assessment and the embedded one or more links, in the primary medical record as a unique document.

15. The system of claim 14, wherein the operations further comprise: receiving a request from a viewing clinician to view the integrated medical consultation report.

16. The system of claim 15, wherein the operations further comprise: accessing the stored integrated medical consultation report with the subjective assessment and the embedded one or more links.

17. The system of claim 16, wherein the operations further comprise: utilizing the embedded one or more links to access and load data for the one or more objective medical factors from the primary medical record into the template.

18. The system of claim 17, wherein the operations further comprise: generating a graphical user interface of the integrated medical consultation report.

19. The system of claim 18, wherein the operations further comprise: generating placeholders on the graphical user interface for data for the one or more objective medical factors from the primary medical record that do not yet have results or values.

20. The system of claim 19, wherein the placeholders are configured to notify the viewing user that the one or more of the objective medical factors from the primary medical record do not yet have results or values.

21. The system of claim 14, wherein the objective medical factors comprise one or more of laboratory results, pathology reports, microbiology reports, genetic test results, infectious disease test results, patient history, patient images, patient physical examination, patient travel history, patient vital sign values, or radiology results.

22. A method, comprising:
generating, while displaying a primary medical record for a patient, a graphical user interface that presents a template usable for creation of:
(a) a subjective assessment, of the patient, by a clinician; and
(b) one or more objective medical factor indicators, corresponding to one or more objective medical factors in the primary medical record, associated with the subjective assessment and considered by the clinician;
receiving first input for the creation of the one or more objective medical factor indicators, and second input for the creation of the subjective assessment, via the graphical user interface;
embedding, in a user-interactive medical consultation report corresponding to the template, one or more links from the one or more objective medical factor indicators to one or more corresponding objective medical factors in the primary medical record; and
storing an integrated medical consultation report, with the subjective assessment and the embedded one or more links, in the primary medical record as a unique document.

23. The method of claim 22, further comprising:
receiving a request from a viewing clinician to view the integrated medical consultation report; and
accessing the stored integrated medical consultation report with the subjective assessment and the embedded one or more links.

24. The media method of claim 23, further comprising: utilizing the embedded one or more links to access and load data for the one or more objective medical factors from the primary medical record into the template.

25. The method of claim 24, further comprising: generating a graphical user interface of the integrated medical consultation report.

* * * * *